United States Patent
Tanaka et al.

(10) Patent No.: US 7,329,123 B2
(45) Date of Patent: Feb. 12, 2008

(54) AIR-DRIVEN CUTTING DEVICE FOR MEDICAL TREATMENT

(75) Inventors: Noriyuki Tanaka, Kyoto (JP); Shozo Nakayama, Kyoto (JP); Hirofumi Jikuhara, Kyoto (JP); Naruo Wada, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 0 days.

(21) Appl. No.: 10/434,909

(22) Filed: May 9, 2003

(65) Prior Publication Data

US 2004/0018467 A1    Jan. 29, 2004

(30) Foreign Application Priority Data

May 10, 2002  (JP) .............................. 2002-135785

(51) Int. Cl.
*A61C 1/05*   (2006.01)
(52) U.S. Cl. ...................... 433/132; 415/904
(58) Field of Classification Search ................ 433/132; 415/904
See application file for complete search history.

(56) References Cited

U.S. PATENT DOCUMENTS 3,156,158 A  *  11/1964  Pamplin ..................... 418/217
4,341,520 A  *  7/1982   Wallace ...................... 433/132
4,913,447 A  *  4/1990   Jostlein ....................... 277/304
5,667,383 A  *  9/1997   Mendoza et al. ............ 433/132
5,807,108 A  *  9/1998   Schwenoha et al. ......... 433/132
6,120,291 A  *  9/2000   Bareth et al. ................ 433/132

FOREIGN PATENT DOCUMENTS

| AT | 372596   | 10/1983 |
|----|----------|---------|
| DE | 1566186  | 2/1972  |
| DE | 69201133 | 8/1995  |

* cited by examiner

*Primary Examiner*—John J Wilson
(74) *Attorney, Agent, or Firm*—William L. Androlia; H. Henry Koda

(57) ABSTRACT

A dental cutting device has a head portion (10) which accommodates a rotary cylinder (20) for holding a cutting tool (22), and a turbine blade (21) mounted around and secured on the rotary cylinder (20). Air fed from an air-supply port (24) is blown onto the turbine blade to rotate the same, and the air blown onto the turbine blade is exhausted from the exhaust port (25). The head portion has a first chamber (26) which is located at a portion confronting the outer peripheral end portion of the turbine blade and which extends in a direction orthogonal to the central axis of the rotary cylinder, and second chambers (27, 28) which are located adjacent to one or both ends of the turbine blade along the direction of the central axial and which communicate with the first chamber.

12 Claims, 5 Drawing Sheets

Figure: Immediately after termination of air supply.

US 7,329,123 B2

AIR-DRIVEN CUTTING DEVICE FOR MEDICAL TREATMENT

RELATED APPLICATION

The present application claims the right of priority under 35 U.S.C. §119 of Japanese Patent Application No. 2002-135785, filed on May 10, 2002.

FIELD OF THE INVENTION

The present invention relates to an air-driven cutting device for a medical treatment such as dental treatment.

RELATED ART

Generally, an air-driven handpiece having a cutting device for medical treatment such as dental treatment has a distal end supporting a head portion to which a necessary cutting tool is removably attached. The head portion accommodates a rotary cylinder or shaft for holding a cutting tool, two bearings for supporting the rotary cylinder, and a turbine blade disposed between the two bearings. The cutting tool is caused to rotate by applying, onto the turbine blade, a compressed air fed from an air-supply passage formed in the grip portion of the handpiece. The grip portion also has an exhaust passage formed therein, through which the compressed air, after being applied to the turbine blade, is discharged.

However, the above air-driven cutting device has a problem in that, even though the feeding of a compressed air is stopped, the rotary cylinder and the turbine blade continue to rotate for a while because of their inertia. This inertial rotation disadvantageously sucks air remaining in small spaces of the head portion pushes and forces it into the air-supply passage and the exhaust passage, causing the spaces to be vacuumed, which is called as "suck-back". This in turn causes an external air to be sucked into the interior of the head portion through the gaps formed on the outer peripheries of the rotary cylinder and the cutting tool. Not only this but also the suck-back causes that the saliva, the blood and tooth debris of a patient are sucked into the interior of the head portion in the course of a dental treatment.

The suck-back has been pointed out so far and various solutions therefor have been proposed. However, each of the proposed solutions is mechanically complicated, and needs more elaboration to be practically applied. Further, there is proposed a system of feeding a compressed air into an air-supply passage and an exhaust passage when the rotation of a cutting tool is stopped. This system, however, requires very complicated mechanism and control for the device.

SUMMARY OF THE INVENTION

Under the foregoing circumstances, the present invention is achieved in order to provide a dental cutting device capable of preventing the above suck-back, by making a simple improvement on a conventional head portion. That is, the present invention provides a dental cutting device which comprises a head portion accommodating a rotary cylinder for holding a cutting tool, and a turbine blade mounted around and secured on the rotary cylinder, and which causes an air fed from an air-supply port to blow onto the turbine blade to rotate the same, and exhausts the air having struck against the turbine blade, from an exhaust port. The feature of this cutting device rests in that the head portion has a first chamber which is located at a portion thereof confronting the outer peripheral end portion of the turbine blade and which extends in a direction orthogonal to the central axis of the rotary cylinder, and a second chamber which is located adjacent to at least one end of the turbine blade along the direction of the above central axis and which communicates with the first chamber.

In another aspect, the present invention provides a dental cutting device comprising a head portion which accommodates a rotary cylinder for holding a cutting tool, two bearings for supporting the rotary cylinder, and a turbine blade mounted around and secured on the rotary cylinder between the two bearings, wherein an air fed from an air-supply port is blown onto the turbine blade to rotate the same, and the air blown onto the turbine blade is exhausted from an exhaust port. The feature of this cutting device rests in that the head portion has a hollow space for accommodating the two bearings and the turbine blade, and that gaps which are formed on both end sides of the rotary cylinder to allow the above hollow space to communicate with an external atmosphere are sealed by sealing members.

In other aspect, the present invention provides a dental cutting device comprising a head portion which accommodates a rotary cylinder for holding a cutting tool, two bearings for supporting the rotary cylinder, and a turbine blade mounted around and secured on the rotary cylinder between the two bearings, wherein an air fed from an air-supply port is blown onto the turbine blade to rotate the same, and the air blown onto the turbine blade is exhausted from an exhaust port. The feature of this cutting device rests in that the head portion has a first chamber which is located at a portion confronting the outer peripheral end portion of the turbine blade and which extends in a direction orthogonal to the central axis of the rotary cylinder; a second chamber which is located adjacent to at least one end of the turbine blade along the direction of the central axis and which communicates with the first chamber; and a sealing member which is located on the other end of the turbine blade along the direction of the central axis so as to seal a gap between the hollow space accommodating the two bearings and the turbine blade, and an external atmosphere.

In any of these dental cutting devices, it is preferable that the sealing member is continuously in contact with the outer peripheral surface of the rotary cylinder or the cutting tool.

PREFERRED EMBODIMENTS OF THE INVENTION

Figure 1:
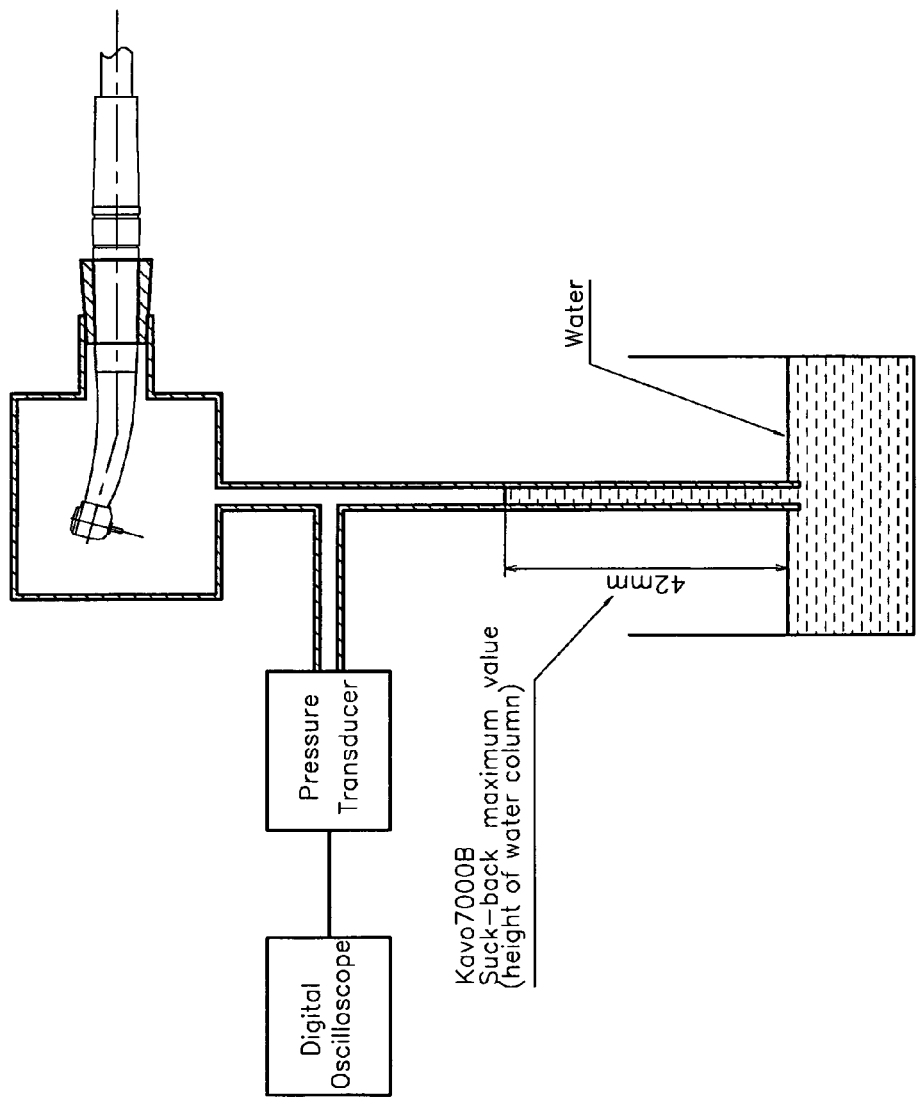
FIG. 1 is an enlarged sectional view of a part of a dental cutting device according to the first embodiment of the present invention.
Figures 2, 3:
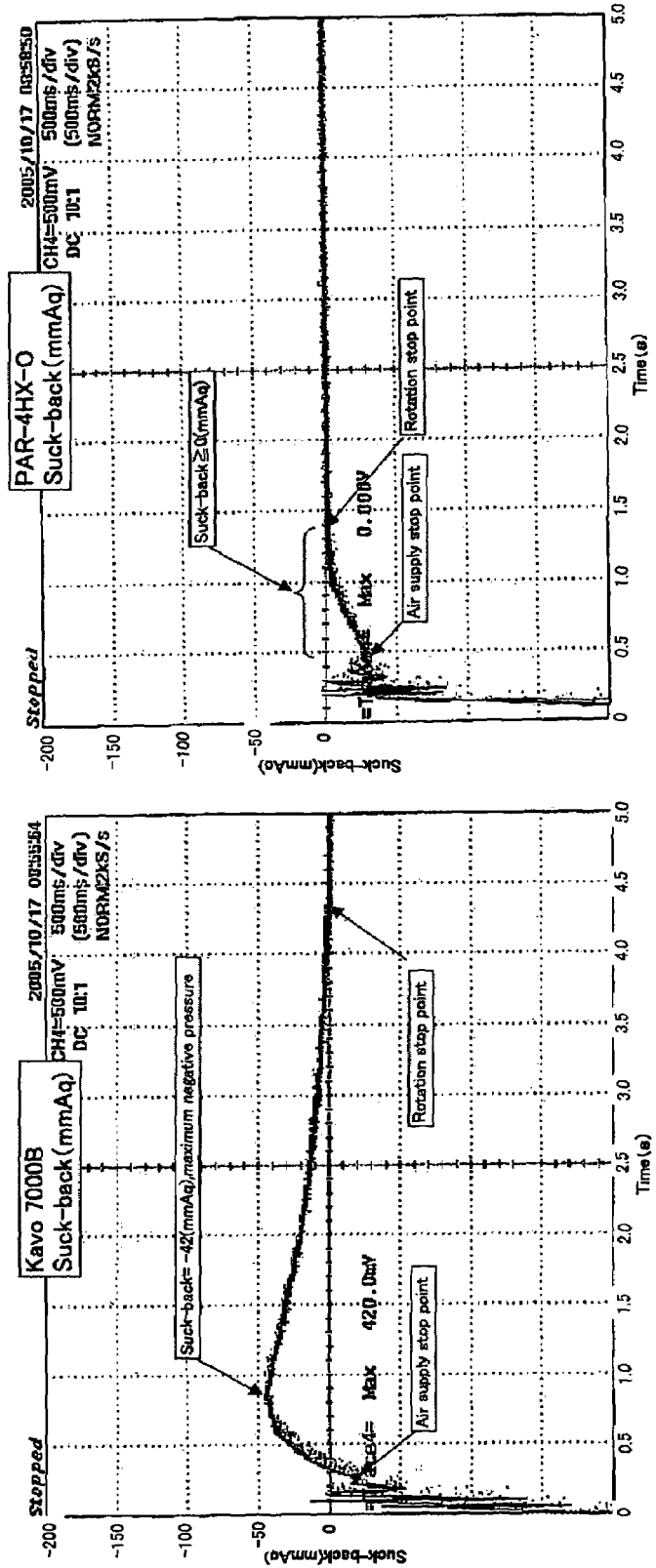
FIG. 2 is a sectional view of the dental cutting device shown in FIG. 1, taken along line II-II.
FIG. 3 is a sectional view of a part of a dental cutting device according to the second embodiment of the present invention.

Referring to FIGS. 1 and 2, a dental handpiece or cutting device according to the present invention, generally indicated by reference numeral (1), has a head portion (10) defined in its distal end of a handpiece (1). The head portion (10) has a shaft section (11) formed on its proximal end and connected to a grip portion (not shown) and a circular housing (12) formed on its distal end.

The housing (12) has a cup-shaped outer housing (13), a cup-shaped inner housing (14) removably accommodated within the outer housing (13), and a top housing (15) disposed on top of the inner housing (14). A hollow space (16) is defined by the inner housing (14) and the top housing (15). An upper bearing (17) and a lower bearing (18) are arranged on the upper and lower sides of the hollow space (16), and are held by the top housing (15) and the inner housing (14), respectively. The upper bearing (17) and the lower bearing (18) rotatably support a rotary cylinder (a rotor shaft) (20) disposed coaxially with the central axis (19) of the housing (12). A turbine blade (21) is mounted on the rotary cylinder (20) between the upper bearing (17) and the lower bearing (18) so that the rotary cylinder (20) with the turbine blade (21) is rotated around the central axis (19). In particular, the lower end portion of the rotary cylinder (20) is projected out of the lowermost end of the outer housing (13) and then exposed to an external through openings defined at the lowermost end portions of the outer and inner housings (13, 14), respectively. Thus, a cutting tool (22) is inserted into the housing through the lower end opening of the rotary cylinder (20). The upper opening of the outer housing (13), on the other hand, is closed by a cap (23) disposed on the top housing (15).

Both air-supply passage (24) and air-exhaust passage (25) are extended through the inner housing (14), the outer housing (13) and then the shaft section (11) connected to the grip portion. As best shown in FIG. 2, the turbine blade (21) of this embodiment is so designed that it rotates clockwise in FIG. 2. Therefore, the air-supply passage (24) is so directed as to inject an air from the upstream side toward the downstream side with respect to the rotating direction. Further, an outer peripheral chamber (a first chamber) (26) confronting the outer peripheral end portion of the turbine blades is formed in a region between the air-supply passage (24) and the exhaust passage (25) so that it extends through the inner housing (14) into the outer housing (13). As best shown in FIG. 1, the outer peripheral chamber (26) has a substantially rectangular cross section on a plane parallel to the central axis (19). Also, as best shown in FIG. 2, the outer peripheral chamber (26) is extended outwardly so that it inclines downwardly with respect to the rotational direction of the turbine blade (21). Preferably, the inclining angle, i.e., an angle θ between a line crossing the central axis (19) and the side wall of the outer peripheral chamber (26) is set about 50 to about 80 degrees. Furthermore, an upper chamber (a second chamber) (27) and a lower chamber (a second chamber) (28) are defined above or below the turbine blade (21), specifically at regions adjacent to both upper and lower end portions of the turbine blade (21) so that they connect with the upper and lower end portions of the outer peripheral chamber (26), respectively.

In operation of the handpiece (1) so constructed, a compressed air is fed through the air-supply passage (24) into the hollow space (16) and then applied to the turbine blade (21), causing the turbine blade (21) to rotate clockwise in FIG. 2. With the rotation of the turbine blade (21), the compressed aid is transported around the axis (19) and then exhausted from the exhaust passage (25). Also, the rotation of the turbine blade (21) is transmitted through the rotary cylinder (20) to the cutting tool (22). Even if the feeding of the compressed air is stopped, the turbine blade (21) continues to rotate for a while due to its inertia. Therefore, the air rotating in the hollow space (16) by the rotation of the turbine blade (21) is forced not only into the air-supply passage (24) and the exhaust passage (25) but also into the outer peripheral chamber (26) with an aid of the centrifugal force. The air in the outer peripheral chamber (26) is thereby compressed. The compressed air in the outer peripheral chamber (26) is then transported into the upper chamber (27) and the lower chamber (28), which communicate with the upper and lower end portions of the outer peripheral chamber (26), respectively, as shown in FIG. 1. Finally, a part of the compressed air is transported through an upper gap (29) between the top housing (15) and; the rotary cylinder (20) and then through the upper bearing (17) into the atmosphere. Simultaneously, another part of the compressed air is transported through a lower gap (30) between the rotary cylinder (20) and the housings (13, 14) and through the lower bearing (18). This results in that the upper gap (29) and the lower gap (30) are practically air-sealed to thereby inhibit the entering of an external air and the saliva and/or blood in the buccal cavity of a patient who is undergoing a dental treatment, into the hollow space (16) of the housing.

Although the handpiece (1) of the this embodiment has the upper chamber (27) defined above the turbine blade (21), it may be omitted if the outer housing (13) is sealed completely by the cap (29).

Also, although the handpiece (1) of this embodiment employs the gear-like turbine blade (21), it may take any configuration and size.

Referring to FIG. 3, there is shown a part of another handpiece or cutting device, generally indicated by reference numeral 101, according to the second embodiment of the present invention. Generally, the handpiece (101) has a grip portion (102) held by an operator and a head portion (103) mounted on the distal end of the grip portion (102). The grip portion (102) has a cylindrical body having an opening at its distal end (the end portion on the left side on the drawing). The head portion (103) has a shaft section (104) inserted into and secured in the distal end opening of the cylindrical body and a housing (105) for accommodating a bearing mechanism described below.

The housing (105) has a cup-shaped outer housing (106) formed integrally with the shaft section (104), a cup-shaped inner housing (107) removably accommodated in the outer housing (106), and an annular top housing (108) fitted in the upper opening of the inner housing (107). A hollow space (109) is formed between the inner housing (107) and the top housing (108). An upper bearing (110) and a lower bearing (111) disposed above and below the hollow space (109) are held by the top housing (108) and the inner housing (107), respectively. The upper bearing (110) and the lower bearing (111) rotatably support a rotary cylinder (a rotor shaft) (113) which is disposed coaxially with the central axis (112) of the housing (105). A turbine blade (114) is mounted on the rotary cylinder (113) between the upper bearing (110) and the lower bearing (111) so that the rotary cylinder (113) and the turbine blade (114) can rotate around the central axis (112). The lower end portion of the rotary cylinder (113) is exposed to an atmosphere through the openings formed on the lower end portions of the outer housing (106) and the inner housing (107), respectively, so that a cutting tool (115) can be inserted into the housing from the lower end of the rotary cylinder (113). Further, a locking ring (116) is removably fitted around the upper opening of the outer housing (106) so as to position the top housing (108) and also to lock a cap (117) for covering the top housing (108).

The turbine blade (114) has an upper blade (118) formed on the peripheral and upper side thereof and a lower blade (119) formed on the peripheral and lower side thereof. A double-blade turbine disclosed in JP 2001-162416 (A) is preferably used for the turbine blade. On the other hand, air-supply passages (120, 121) are formed in the inner housing (107) and the shaft section (104) so that they communicate with each other to confront the upper blade (118). Exhaust passages (122, 123) are formed in the inner housing (107) and the shaft section (104) so that they communicate with each other to confront the lower blade (119). Further, an air passage (124) which connects the upper blade (118) to the lower blade (119) through a fluid is formed in the interior of the inner housing (107).

Figure 4:
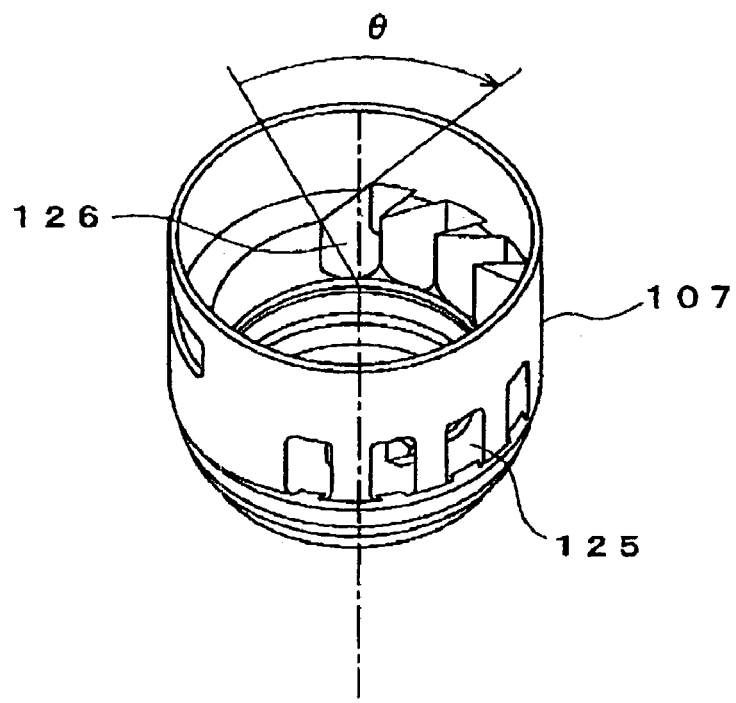
FIG. 4 is a perspective view of an inner housing.
Figure 5:
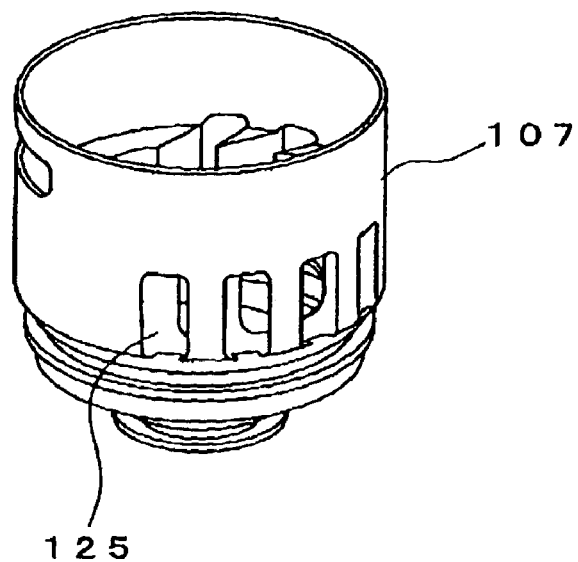
FIG. 5 is a perspective view of an inner housing.

A plurality of outer peripheral chambers (first chambers) (125) passing through the inner housing (107) are formed in the inner housing (107) so that they confront the outer peripheral end portions of the lower blade (119). The outer peripheral chambers (125) can easily be machined externally because they fully extend through the inner housing (107). As best shown in FIGS. 4 and 5, the turbine blade (114) is so designed that it rotates in the clockwise direction, and therefore, the outer peripheral chambers (125) are extended radially toward the downstream with respect to the rotating direction of the turbine blade (114). Preferably, the inclining angle, i.e., the intersection angle θ between the central axis (112) and the side wall (126) of the outer peripheral chamber (125) is specifically set at about 50 to about 80 degrees. Further, lower chambers (second chambers) (127) are formed below the turbine blade (114), specifically in the regions adjacent to the lower end portion of the turbine blade so that they confront the lower sides of the outer peripheral chambers (125).

On the other hand, an annular groove (128) surrounding and confronting the outer peripheral surface of the rotary cylinder (113) is formed between the top housing (108) and the upper bearing (110). An annular elastic seal (a lip packing) (129) (see FIG. 6) received in the annular groove (128) seals a gap between the top housing (108) and the rotary cylinder (113).

Figure 6:
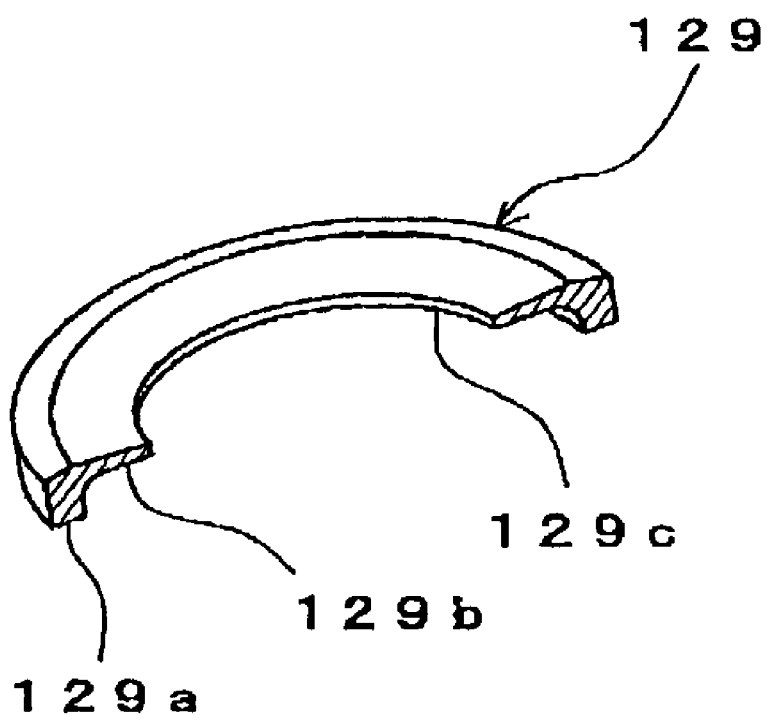
FIG. 6 is a perspective view of a part of an annular seal.
Figure 7:
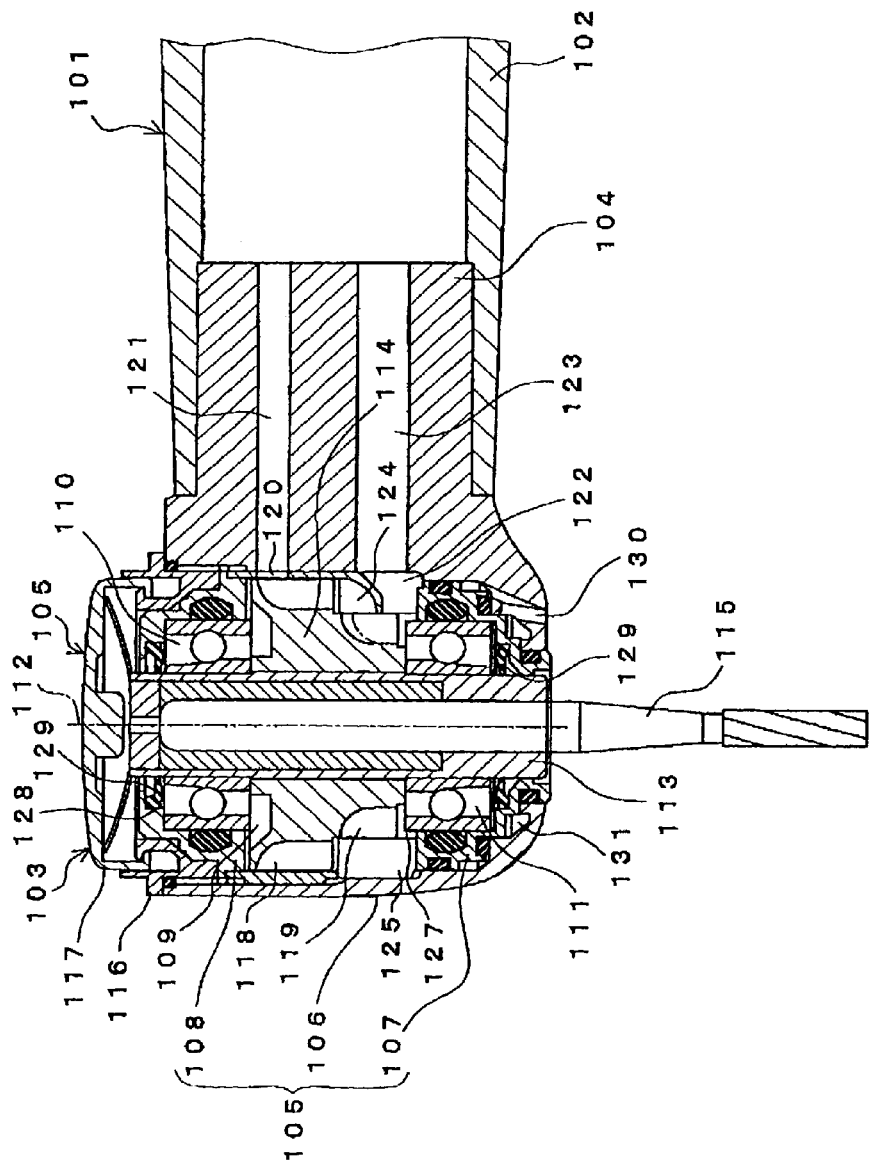
FIG. 7 is a sectional view of a part of a dental cutting device according to the third embodiment of the present invention.

In this embodiment, as shown in FIG. 6 the lip packing (129) is a rubber-molded sealing member with an annular base portion (129a) and a thin-wall portion (129b) extending inwardly in the radial direction from the inner circumference of the annular base portion (129a). The thin-wall portion (129b) is so formed that the thickness thereof is gradually reduced toward the inner circumferential end (129c) having an inner diameter slightly smaller than the outer diameter of the rotary cylinder (113). As shown in FIG. 7, the lip packing (129) disposed on the upper bearing (110) is in contact with the outer peripheral surface of the rotary cylinder (113) with its inner circumferential end portion (129c) facing upward, and another lip packing (129) disposed underneath the lower bearing (111) is received in the annular groove (128) as it keeps in contact with the outer peripheral surface of the rotary cylinder (113) with its inner circumferential end portion (129c) facing downward. Accordingly, while the compressed air is fed into the hollow space (109) to raise the internal pressure thereof, the inner circumferential end portion (129c) of the lip packing (129) easily deforms outwardly, and leaves from the rotary cylinder (114). Thus, the compressed air in the hollow space (109) outflows to an external atmosphere through a gap formed between the deformed inner circumferential end portion (129c) and the rotary cylinder (114). Therefore, the rotary cylinder (114) does not receive a resistance from the lip packing (129) while being rotated, and thus, normal rotation can be ensured.

In addition, a plurality of water-injecting holes (130) are formed at regular intervals on the base portion of the outer housing (106). The water-injecting holes (130) are connected to one another through an annular water passage (131) formed on the inner surface of the outer housing (106) which confronts the inner housing (107), and are also connected to a water-feeding passage (not shown) in the shaft section (104).

In operation of the handpiece (101) so constructed, water fed through a water-feeding tube (not shown) accommodated in the grip portion (102) is injected from the plurality of water-injecting holes (130) onto the distal end of the cutting tool (115), through the water-feeding passage in the shaft section (104) and the annular water passage (131) in the housing (105). On the other hand, a compressed air fed through an air-supply tube (not shown) accommodated in the grip portion (102) is blown onto the upper blade (118) of the turbine blade (114) through the air-supply passages (121, 120) of the shaft section (104) and the inner housing (107) The compressed air blown onto the upper blade (118) is then applied onto the lower blade (119) through the air passage (124). Consequently, the turbine blade (114) is rotated, and simultaneously, the rotary cylinder (113) equipped with this turbine blade (114) is rotated. Also, the cutting tool (115) held by the rotary cylinder (113) is rotated.

When the feeding of the compressed air is stopped, the force of rotating the turbine blade (114) is ceased. However, the turbine blade (114) continues to rotate due to its inertia. Therefore, the air which moves in the hollow space (109) with the rotation of the turbine blade (114) is forcedly sent not only into the air-supply passages (120, 121) and the exhaust passages (123, 124) but also into the outer peripheral chambers (125) by the centrifugal force. The air compressed in the outer peripheral chambers (125) is transported into the lower chambers (127) adjacent to the lower end surface of the outer peripheral chambers (125), and then released through the lower gap between the inner housing (107) and the rotary cylinder (113) into the atmosphere. The lower gap is therefore practically air-sealed to inhibit the entering of an atmospheric air, the saliva, the blood of the buccal cavity of a patient who is undergoing a dental treatment, into the hollow space (109) of the head portion. Further, since the annular seal (129) seals the gap between the top housing (108) and the rotary cylinder (113), an external air can not enter the hollow space (109) through such a gap. Further, the annular seal (129) is mechanically in contact with the rotary cylinder (113) to prevent the inertial rotation of the turbine blade (114). Therefore, the period during which a negative pressure occurs in the hollow space (109) becomes shorter, which substantially prevents the occurrence of the suck-back. In addition, when the feeding of the compressed air is stopped, the annular seal (129) comes into contact with the rotary cylinder (113) to quickly stop the turbine blade (114).

Although the annular seal (129) is provided only between the top housing (108) and the rotary cylinder (113), as shown in FIG. 7 another annular seal (129) may be provided on the lower side of the lower bearing (111) so as to seal a gap between the inner housing (107) and the rotary cylinder (113). Thus, in combination with the above air seal, an external air can be prevented from entering through the gap between the inner housing (107) and the rotary cylinder (113).

Also, regardless of that the second chamber is adjacent to the lower end portion and/or the upper end portion of the turbine blade, the endless seal may be positioned on the upper side and/or the lower side of the rotational cylinder.

As can be seen from the foregoing description, according to the present invention, it is possible to effectively prevent the entering of the saliva or the like of a patient into the head portion due to the suck-back which would arise when the rotation of a turbine blade is stopped, without the need of complicated adaptation of the head portion.

What is claimed is:

1. An air-driven cutting device for a medical treatment, the cutting device comprising:
   a hand piece including a head portion receiving a rotary cylinder for holding a cutting tool and a turbine blade mounted around and secured on the rotary cylinder so that an air fed from an air-supply by an air-supply passage is applied onto the turbine blade to rotate the turbine blade and then exhausted from an exhaust passage;
   wherein the head portion has
      a first chamber which is located at a portion confronting the outer peripheral end portion of the turbine blade and which extends in a direction orthogonal to the central axis of the rotary cylinder and between the air-supply passage and the exhaust passage as said air-supply and exhaust passage run through said had piece, and
      at least one second chamber which is located adjacent to at least one end of the turbine blade along an axial direction of the turbine blade and which communicates with the first chamber, and
   wherein the first chamber is formed inclining in the rotating direction of the turban blade relative to a line orthogonal to the central axis.

2. The device of claim 1, wherein a plurality of first chambers are formed.

3. The device of claim 1 or 2, wherein the first chamber has a substantially rectangular section on a plane in parallel to the central axis.

4. The device of claim 1, wherein the head portion comprises an outer housing and an inner housing removably fitted in the outer housing, and the first chamber is formed in the inner housing.

5. The device of claim 4, wherein the first chamber is formed passing through the inner housing.

6. The device of claim 1, wherein said second chamber is provided above and below a top and a bottom, respectively, of said turbine blade.

7. The device of claim 6, wherein said second chamber provided above said top of said turbine blade communicates with a top of said first chamber and said second chamber provided below said bottom of said turbine blade communicates with a bottom of said first chamber.

8. An air-driven cutting device for a medical treatment, the cutting device comprising:
   a hand piece including a head portion which accommodates a rotary cylinder for holding a cutting tool,
   two bearings for supporting the rotary cylinder; and a turbine blade mounted around and secured on the rotary cylinder between the two bearings,
   wherein an air fed from an air-supply passage is blown onto the turbine blade to rotate the turbine blade, and the air blown onto the turbine blade is exhausted from an exhaust passage,
   wherein the head portion has
      a first chamber which is located at a portion confronting the outer peripheral end portion of the turbine blade and which extends in a direction orthogonal to the central axis of the rotary cylinder and between the air-supply passage and the exhaust passage as said air-supply and exhaust passage run through said hand piece,
      a second chamber which is located adjacent to at least a bottom or a top end of the turbine blade along an axial direction of the turbine blade and which communicates with the first chamber, and
      a sealing member which is located at one side of the other end of the turbine blade along the direction of the central axis to seal a gap between the hollow space accommodating the two bearings and the turbine blade, and an external atmosphere and each of the sealing members makes a direct and sealing contact with an outer periphery of said rotary cylinder, and
   wherein the first chamber is formed inclining in the rotating direction of the turbine blade relative to a line orthogonal to the central axis.

9. The device of claim 8, wherein a plurality of first chambers are formed.

10. The device of claim 8, wherein the first chamber has a substantially rectangular section on a plane in parallel to the central axis.

11. The device of claim 8, wherein the head portion comprises an outer housing and an inner housing removably fitted in the outer housing, and the first chamber is formed in the inner housing.

12. The device of claim 11, wherein the first chamber is formed passing through the inner housing.

* * * * *